United States Patent [19]

Hanson

[11] Patent Number: 6,093,819
[45] Date of Patent: *Jul. 25, 2000

[54] PREPARATION OF PENCICLOVIR OR FAMCICLOVIR

[75] Inventor: John Christopher Hanson, Epsom, United Kingdom

[73] Assignee: SmithKline Beecham plc, Harlow, United Kingdom

[ * ] Notice: This patent is subject to a terminal disclaimer.

[21] Appl. No.: 09/261,609

[22] Filed: Feb. 26, 1999

Related U.S. Application Data

[62] Division of application No. 08/409,490, Mar. 21, 1995, Pat. No. 5,910,589, which is a continuation of application No. 08/094,132, filed as application No. PCT/GB92/00177, Jan. 30, 1992.

[30] Foreign Application Priority Data

Jan. 31, 1991 [GB] United Kingdom ................... 9102127

[51] Int. Cl.⁷ ....................... C07D 473/18; C07D 473/32
[52] U.S. Cl. ............................................. 544/276; 544/277
[58] Field of Search ...................... 544/277, 276

[56] References Cited

U.S. PATENT DOCUMENTS

| 4,736,029 | 4/1988 | Harnden et al. ...................... 544/267 |
|---|---|---|
| 5,075,445 | 12/1991 | Jarvest et al. ...................... 544/276 |
| 5,216,161 | 6/1993 | Hanson ...................... 544/322 |
| 5,389,637 | 2/1995 | Igi ...................... 544/277 |
| 5,434,263 | 7/1995 | Hertzsch ...................... 544/264 |
| 5,910,589 | 6/1999 | Hanson ...................... 544/277 |

FOREIGN PATENT DOCUMENTS

| 0 141 927 | 5/1985 | European Pat. Off. . |
|---|---|---|
| 0 182 024 | 5/1986 | European Pat. Off. . |
| 0 203 685 | 12/1986 | European Pat. Off. . |
| 0 433 846 | 6/1991 | European Pat. Off. . |
| 9 101 310 | 2/1991 | WIPO . |

OTHER PUBLICATIONS

Secrist et al., "2–Fluoroformycin and 2–Aminoformycin. Synthesis and Biological Activity", J. Med. Chem., 28, pp. 1740–1742 (1985).
Translation of EP 433845 (1991).
Abstract of WO92/ 13859 (1992).

*Primary Examiner*—Mark L. Berch
*Attorney, Agent, or Firm*—Dara L. Dinner; Stephen Venetianer; Charles M. Kinzig

[57] ABSTRACT

A process for preparing 2-amino-6-chloropurine or a 2-acylated derivative thereof, comprising reacting guanine or 2,9-diacylguanine with a chlorinating agent, in the presence of methyltriethylammonium chloride as phase transfer catalyst, and thereafter when necessary, removing the 9-acyl group by hydrolysis.

5 Claims, No Drawings

PREPARATION OF PENCICLOVIR OR FAMCICLOVIR

This is a divisional of application Ser. No. 08/409,490 U.S. Pat. No. 5,910,589 filed Mar. 21, 1995, which is a continuation of application Ser. No. 08/094,132 filed Jul. 30, 1993, which is a 371 of PCT/GB92/00177 filed Jan. 30, 1992.

This invention relates to a process for the preparation of a compound useful as an intermediate in the preparation of pharmaceutical compounds.

The compound 2-amino-6-chloropurine of formula (I):

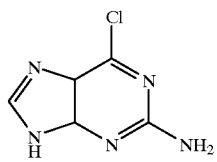

(I)

is a useful intermediate in the preparation of nucleoside analogue antiviral agents, such as penciclovir and famciclovir, described in EP-A-141927 (Example 1) and EP-A-182024 (Example 2). The intermediate is 9-substituted with an appropriate side chain precursor, followed by conversion of the 6-chloro moiety to a hydroxy (a guanine) or hydrogen (a 2-aminopurine).

EP-A-203685 (Beecham Group p.l.c.) describes a process for preparing a compound of formula (I) as hereinbefore defined, which process comprises reacting guanine with a chlorinating agent in the presence of a phase transfer catalyst containing chloride ions. EP-A-433846 (Hoechst Aktiengesellschaft) describes a corresponding process for preparing the 2-acylated derivative, involving chlorination of 2,9-diacylguanine and subsequent removal of the 9-acyl group by hydrolysis.

The reaction is preferably carried out in a polar inert organic solvent such as acetonitrile, tetrahydrofuran, dioxan, nitromethane, diglyme or dimethoxyethane. Acetonitrile is highly preferred.

Suitable phase transfer catalysts include tetrasubstituted ammonium chlorides. Examples of ammonium substituents include $C_{2-12}$ alkyl, usually $C_{2-4}$ alkyl, or phenyl or benzyl. Other possible phase transfer catalysts include tetra-substituted phosphonium chlorides wherein examples of the substitutents are as defined above for ammonium chlorides. The preferred phase transfer catalyst used was tetraethylammonium chloride.

The phase-transfer catalyst is preferably present in an amount of from 1 to 3 equivalents of the compound of formula (II) and preferably from 1 to 2 equivalents.

A preferred chlorinating agent is phosphorus oxychloride.

Preferably the chlorinating agent is present in an amount of from 2–10 preferably from 3–6 molar equivalents of the compound of formula (I).

The reaction may be effected in the presence of a weak base, such as a tertiary amine, for example N,N-dimethylaniline or diethylaniline. The base is usually present in an approximately molar equivalent amount with respect to the compound of formula (I). Alternatively, a catalytic amount of water may be added to the reaction mixture. When acetonitrile is the solvent, added base is not necessary.

The reaction is preferably carried out at an elevated temperature of from 30–100° C., most preferably under reflux and/or with ultrasonication at 60–70° C.

Preferably the reaction is allowed to proceed for a period of greater than half an hour, usually less than 30 hours.

Surprisingly, we have now discovered that the preferred phase transfer catalyst is methyltriethylammonium chloride (TEMAC).

Accordingly, the present invention provides a process for preparing 2-amino-6-chloropurine or a 2-acylated derivative thereof, which process comprises reacting guanine or a 2,9-diacylated derivative thereof, with a chlorinating agent in the presence of TEMAC, and thereafter when necessary, removing the 9-acyl group by hydrolysis.

All other aspects of the process are as described in EP-A-203685 and EP-A-433846.

The following examples illustrate the invention.

EXAMPLE 1

2-Amino-6-chloropurine

A mixture of guanine (22.7 g, 0.15 mol), methyltriethylammonium chloride (TEMAC) (45.5 g, 0.3 mol), phosphorus oxychloride (82.6 ml, 0.9 mol) and acetonitrile (67 ml) was heated at 60° C. with stirring for 6 hours and then cooled to 10° C. The solid material was filtered off and suspended in water (300 mls). The aqueous mixture was brought to alkaline pH with aqueous sodium hydroxide to achieve dissolution and powdered carbon (6.8 g) added. The mixture was stirred for 1 hour and then filtered to remove the carbon. Acetone (72 mls) was added and then the pH reduced to 7 with dilute hydrochloric acid. The product was filtered off, washed with acetone/water (50:50 mixture, 50 mls), water (50 mls), acetone/water (50:50 mixture, 50 mls) and acetone (50 mls) and then dried to give 2-amino-6-chloropurine as a cream coloured solid (14.77 g, 54% yield).

EXAMPLE 2

2-Acetylamino-6-chloropurine

Diacetyl guanine (16.0 g, 0.068 moles), TEMAC (20.60 g, 0.136 moles), triethylamine (9.48 mls, 0.068 moles) and acetonitrile (80 mls) were heated with stirring to 45° C. and stirred for 15 minutes. Phosphorous oxychloride (12.68 mls, 0.136 moles) was added and the temperature raised to 60° C. The reaction mixture was then stirred at 60–62° C. for 2½ hours. The reaction mixture was then cooled to below 30° C. and added to sodium hydroxide solution (21.8 g, 0.545 moles, in 400 mls water) with stirring. The temperature rose to 58° C. The reaction mixture was heated and acetonitrile, triethylamine and water (135 mls total) distilled out until the head temperature reached 100° C. the liquor was then cooled and the product filtered off and washed with water (20 mls). The product was then dried under vacuum at 80° C. for 3 days (12.695 g, 88% yield).

What is claimed is:

1. A process for preparing for penciclovir or famciclovir, comprising preparing 2-amino-6-chloropurine by reacting guanine with a chlorinating agent in the presence of TEMAC, in a solvent; substituting said 2-amino-6-chloropurine at the 9-position with an appropriate side chain precursor, followed by hydrolysis or reduction of the 6-chloro moiety to hydroxy or hydrogen to provide penciclovir or famciclovir.

2. A process according to claim 1 wherein the chlorinating agent is phosphorus oxychloride.

3. A process according to claim 1 wherein the chlorinating agent is present in an amount of 3 to 6 molar equivalents.

4. A process according to claim 1 wherein the TEMAC is present in an amount of 1 to 2 molar equivalents.

5. A process according to claim 1 wherein the preparation of the 2-amino-chloropurine is carried out in acetonitrile as solvent.

* * * * *